United States Patent [19]

Nogami et al.

[11] Patent Number: 5,432,034
[45] Date of Patent: Jul. 11, 1995

[54] PHOTOCONDUCTOR FOR ELECTROPHOTOGRAPHY INCLUDING AN UNDERCOATING LAYER

[75] Inventors: Sumitaka Nogami; Yasushi Iguchi, both of Kawasaki, Japan

[73] Assignee: Fuji Electric Co., Ltd., Kanagawa, Japan

[21] Appl. No.: 181,108

[22] Filed: Jan. 13, 1994

[30] Foreign Application Priority Data

Jan. 14, 1993 [JP] Japan .................................. 5-004405

[51] Int. Cl.$^6$ .............................................. G03G 5/14
[52] U.S. Cl. ........................................ 430/58; 430/60; 430/63
[58] Field of Search ................... 430/58, 59, 60, 63

[56] References Cited

U.S. PATENT DOCUMENTS 5,075,189 12/1991 Ichino et al. ........................ 430/60
5,279,917 1/1994 Aizawa et al. ...................... 430/60

FOREIGN PATENT DOCUMENTS 48-4382   2/1973 Japan .
58-45707  10/1983 Japan .
60-168157A 8/1985 Japan .
63-101853A 5/1988 Japan .

Primary Examiner—John Goodrow
Attorney, Agent, or Firm—Spencer, Frank & Schneider

[57] ABSTRACT

An organic photosensitive member for electrophotography is provided which comprises a photosensitive layer 3 formed on an electroconductive substrate 1 via an undercoating layer 2, the photosensitive layer 3 comprising a charge generating layer 4 and a charge transporting layer 5, wherein the undercoating layer 2 consists essentially of 12/6/66 copolymeric polyamide expressed by the general formula (I)

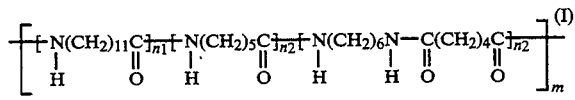

and a styrene/maleic acid half ester copolymer. By providing such an undercoating layer, it becomes possible to obtain a photosensitive member having excellent electrophotographic characteristics, involving minimal changes in these characteristics during repeated use, and giving a high quality image stably.

8 Claims, 1 Drawing Sheet

PHOTOCONDUCTOR FOR ELECTROPHOTOGRAPHY INCLUDING AN UNDERCOATING LAYER

BACKGROUND OF THE INVENTION

1. Field of the Invention

The present invention relates to an organic photosensitive member for use in electrophotographic instruments such as copying machines and various printers.

2. Description of the Prior Art

In recent years, electrophotographic technologies have been widely used not only in the field of copying machines, but also in the field of various printers, because of their instantaneity and high image quality.

Photosensitive members for electrophotography (may hereinafter referred to as "photosensitive members"), which are the core of electrophotographic technologies, have so far been typified by inorganic photosensitive members using inorganic materials such as selenium, arsenic-selenium alloys, cadmium sulfide, and zinc oxide. Recently, organic photosensitive members using organic materials, which are pollution-free and advantageous in terms of facilitated film formation and production, flexibility, light weight, and usability of wide varieties, have been developed and put to practical use.

Organic photosensitive members include so-called laminate type photosensitive members having a photosensitive layer comprising a laminate of a charge generating layer and a charge transporting layer. The laminate type photosensitive members have many advantages such that highly efficient charge generating substances and charge transporting substances may be selected and combined so as to impart high sensitivity, that wide varieties of highly safe materials can be selected, and that film formation can be performed by coating, thus leading to high productivity at lower prices. Since the laminate type photosensitive members are highly likely to become predominant photosensitive members, they are under eager research and development.

A photosensitive member is usually constructed by providing a photosensitive layer on an electroconductive substrate made of aluminum or the like. The surface condition of the substrate greatly affects the characteristics of the photosensitive member. Dirt, foreign matter or scar on the surface of the substrate affects electrophotographic characteristics, possibly causing an image defect. To eliminate such a defect on the substrate surface, surface roughening or mirror finishing is applied to the surface. In many cases, however, the aluminum for use as the substrate is an aluminum alloy containing Mg or Mn. No matter what precision finishing the substrate is subjected to, its surface involves a defect such as a burr or tipping due to the crystallization of the metal incorporated. In addition, aluminum is a chemically active element, so that the surface of the substrate finished tends to be oxidized. Since the oxidation does not proceed uniformly, the resulting oxide film has irregularities, and the substrate surface differs in activity from portion to portion. If a photosensitive layer is provided on such substrate surface, the photosensitive layer has uneven thicknesses, and a layer defect such as a void or crater may easily occur, thus degrading the quality of the resulting image. As a measure for eliminating such influences of the substrate surface, it has been practiced to provide an undercoating layer on the substrate surface. Known examples of the undercoating layer include an inorganic layer of an aluminum anode oxide film, aluminum oxide or aluminum hydroxide, and an organic layer of polyvinyl alcohol, casein, polyvinyl pyrrolidone, polyacrylic acid, cellulose, gelatin, starch, polyurethane, polyimide, or polyamide.

It is well known to use an alcohol-soluble polyamide for an undercoating layer. For example, Japanese Patent Application Publication No. 4382/1973, Japanese Patent Application Publication No. 45707/1983, and Japanese Patent Application Laying-Open No. 168157/1985 disclose the formation of an undercoating layer from an alcohol-soluble polyamide resin. Japanese Patent Application Laying-Open No. 101853/1988 discloses an undercoating layer consisting essentially of an alcohol-soluble polyamide and further containing a water-soluble polyamide.

A first property required of the undercoating layer is to exert no adverse influence on electrophotographic characteristics. To fulfill this requirement, the undercoating layer must have low electric resistance, and the electric resistance must not vary according to the change of the environment. A second requirement is the lack of the function to inject carriers into the charge generating layer. An undercoating layer having the function to inject carriers into the charge generating layer decreases charge potential, thereby causing a decrease in image contrast and inducing a fog. A third requirement is that the undercoating layer can be as thick as possible in order to cover up various defects on the substrate surface. Moreover, the thick layer must keep a good adhesion to the substrate surface. As a fourth requirement, when the undercoating layer is to be formed by a coating process, the coating fluid must be stable.

The undercoating layers so far known have not been entirely satisfactory in fulfilling the above requirements. The use of the aforementioned alcohol-soluble polyamide as the undercoating layer, for instance, has been defective in that it adversely affects the electrophotographic characteristics. The use of an azo pigment as a charge generating substance in the charge generating layer, in particular, has exerted markedly adverse influences on properties such as photosensitivity and residual potential, and has deteriorated image quality.

SUMMARY OF THE INVENTION

The present invention has been accomplished in the light of the above-mentioned drawbacks. Its subject is to provide an organic photosensitive member having excellent electrophotographic characteristics, involving minimal changes in these characteristics during repeated use, and giving a high quality image stably, by disposing an undercoating layer comprising particular materials.

We, the present inventors, have conducted eager studies on various polyamides as materials for an undercoating layer that satisfies the aforementioned requirements. These studies have led us to the finding that so-called 12/6/66 polyamide, prepared by adding equivalent amounts of caprolactam and hexamethylenediamine adipic acid salt to lauric lactam, followed by copolymerizing them, is suitable for the undercoating layer. Preferably, the mixture to be copolymerized comprises 10 to 50 mol % of lauric lactam and the remaining 90 to 50 mol % of caprolactam and hexamethylenediamine adipate in equivalent amounts. This polyamide can be synthesized by a known method, and its examples include DAIAMID T-171 (DAICEL-HÜLS LTD.).

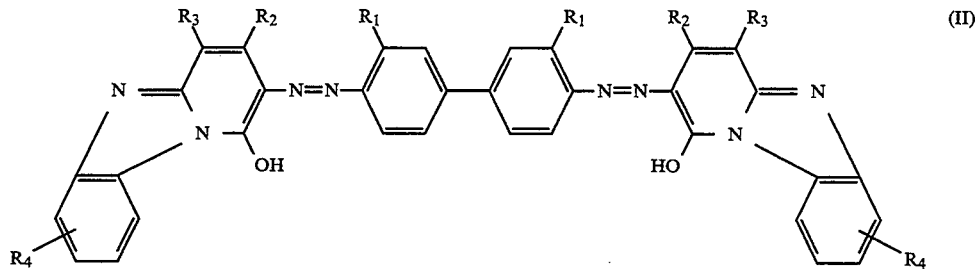

Research has also been conducted on various additives intended to improve adhesion between the substrate and the photosensitive layer. A copolymer of styrene with maleic acid half ester has been found to be completely compatible with the above-described polyamide, thereby improving adhesion, and surprisingly, markedly improving sensitivity. The amount of the styrene-maleic acid half ester copolymer added is preferably within the range of from 1% by weight to 30% by weight based on the undercoating layer, because an amount of less than 1% by weight will not result in sufficient effectiveness, while an amount in excess of 30% by weight will deteriorate the film-forming property. The styrene-maleic acid half ester copolymer can be synthesized by radical polymerization of styrene and maleic acid half ester in a known manner, but may be commercially available as Sprapal AP-20 (BASF).

By providing an undercoating layer containing an alcohol-soluble copolymeric polyamide and styrene-maleic acid half ester copolymer as mentioned above, it becomes possible to obtain a photosensitive member having excellent electrophotographic characteristics, involving minimal changes in these characteristics during repeated use, and giving a high quality image stably.

Hence, the subject of the present invention can be achieved by an organic photosensitive member comprising a photosensitive layer formed on an electroconductive substrate via an undercoating layer, the photosensitive layer containing a charge generating layer and a charge transporting layer, wherein the undercoating layer comprises 12/6/66 copolymeric polyamide expressed by the general formula (I)

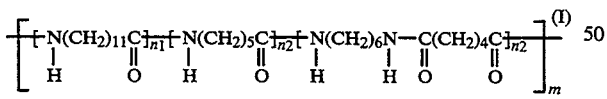

wherein $n_1$ denotes an integer of 10 to 50, $n_2$ denotes an integer of 25 to 45, and m denotes an integer of 1 to 20, and a copolymer of styrene with maleic acid half ester.

In the undercoating layer, it is desirable that the 12/6/66 copolymeric polyamide of the general formula (I) be incorporated in an amount of from 70 to 99% by weight.

Preferred examples of the charge generating substance of the charge generating layer, a constituent of the photosensitive layer, include azo compounds of the general formula (II), polycyclic quinone compounds of the general formula (III), azo compounds of the general formula (IV), and azo compounds of the general formula (V). The coupler residue in the azo compounds of the general formula (IV) and in the azo compounds of the general formula (V) is that in compounds of the general formula (VI).

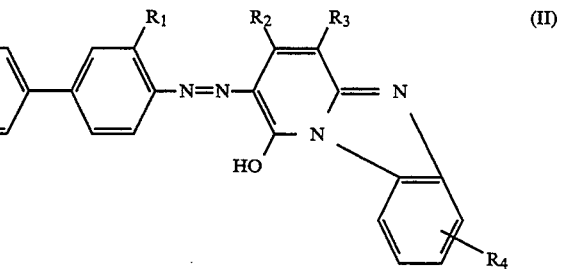

wherein $R_1$ represents a halogen atom, an alkyl group or an alkoxy group, $R_2$ represents an optionally substituted alkyl group, $R_3$ represents a hydrogen atom, a cyano group, a carbamoyl group, a carboxyl group, an ester group or an acyl group, and $R_4$ represents a hydrogen atom, a halogen atom, a nitro group, an alkyl group or an alkoxy group.

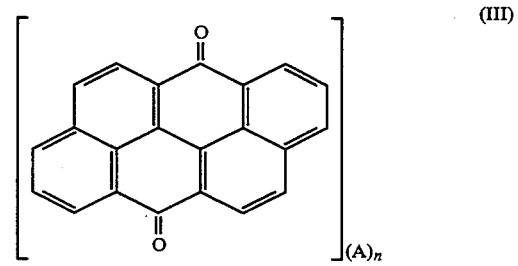

wherein A represents a halogen atom, a nitro group, a cyano group, an acyl group or a carboxyl group, and n denotes an integer of 0 to 4.

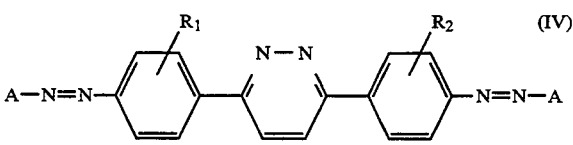

wherein A represents a coupler residue, and $R_1$ and $R_2$ each represent a hydrogen atom, a halogen atom, or an optionally substituted alkyl or alkoxy group.

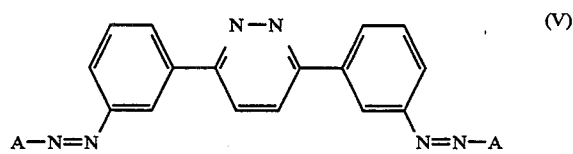

wherein A represents a coupler residue.

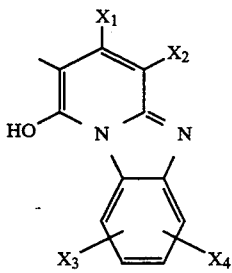

(VI)

wherein $X_1$ represents an optionally substituted alkyl, aryl or heterocyclic group, $X_2$ represents a hydrogen atom, a cyano group, a carbamoyl group, a carboxyl group, an ester group, or an acyl group, and $X_3$ and $X_4$ each represent a hydrogen atom, a halogen atom, a nitro group, or an optionally substituted alkyl or alkoxy group.

The above and other objects, effects, features and advantages of the present invention will become more apparent from the following description of embodiments thereof taken in conjunction with the accompanying drawing.

DETAILED DESCRIPTION OF PREFERRED EMBODIMENTS

Figure 1:
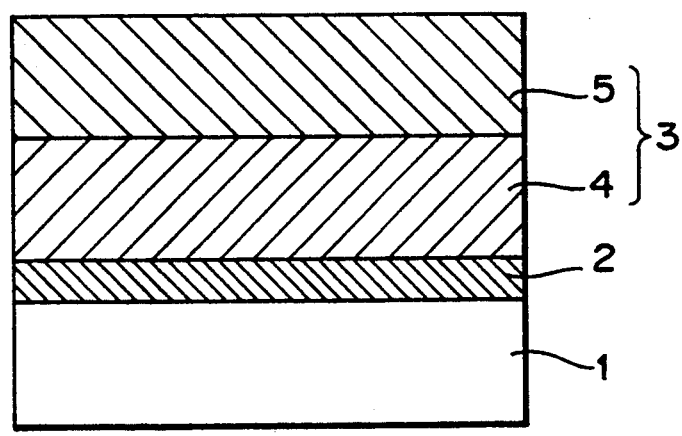
FIG. 1 is a schematic cross sectional view showing an embodiment of a photosensitive member according to the present invention.

FIG. 1 is a schematic cross sectional view showing an embodiment of a photosensitive member according to the present invention. As shown in the drawing, the photosensitive member of the present invention comprises a photosensitive layer 3 formed on an electroconductive substrate 1 via an undercoating layer 2, the photosensitive layer 3 comprising a charge generating layer 4 and a charge transporting layer 5.

The electroconductive substrate 1 is, say, a metallic material, such as aluminum, stainless steel or nickel, a polyester film, a paper sheet, or a glass sheet, each having an electroconductive layer of aluminum, tin oxide or indium oxide on a surface thereof. An aluminum pipe is particularly preferred.

The undercoating layer 2 consists essentially of alcohol-soluble 12/6/66 copolymeric polyamide of the general formula (I) and a styrene-maleic acid half ester copolymer. The undercoating layer 2 is formed by applying a coating solution of the two components dissolved in a solvent. The solvent for the coating solution is an alcohol such as methanol, ethanol, propanol or butanol, or a halogenated hydrocarbon such as methylene chloride, dichloroethane or trichloroethylene, which may be used alone or in combination. From the viewpoint of solution stability, the use of the alcohol is desirable. If desired, various additives may be incorporated in the undercoating layer 2. Examples of the additives are zinc oxide, titanium oxide, aluminum oxide, silicon oxide, silicone oil for improving coating properties, and fluorine derived surface active agents. The thickness of the undercoating layer is preferably 0.05 to 20 μm, more preferably 0.05 to 10 μm.

On the undercoating layer 2 is formed the photosensitive layer 3 comprising the charge generating layer 4 and the charge transporting layer 5. The photosensitive layer may be of a single layer type or a laminate type. The laminate type enables the effect of the present invention to be exhibited markedly.

In the case of the laminate type, charge generating substances for use in the charge generating layer 4 include, for example, inorganic photoconductive materials such as selenium, selenium alloys and cadmium sulfide; and organic pigments such as phthalocyanine pigments, azo pigments, diazo pigments, trisazo pigments, squalilium pigments, pyrylium pigments, perylene pigments and anthanthrone pigments. When the azo pigments of the general formula (II), (IV) or (V) and the polycyclic quinone compounds of the general formula (III) are used, the effect of the invention can be exhibited remarkably. The charge generating layer is formed by applying a coating fluid of any of these pigments dispersed or dissolved in the solvent together with a binder. The binder may be any substance which is electrically insulating and has a film forming capacity. Preferred examples of such binder are polyvinyl ketal resins such as polyvinyl formal, polyvinyl acetal or polyvinyl butyral, acrylic resins, styrene resins, polyester resins, polycarbonate resins, vinyl chloride resins, vinyl acetate resins, and silicone resins. The amount of any of these binders is preferably within the range of from 10 to 300% by weight based on the charge generating substance. The thickness of the charge generating layer is preferably 0.01 to 2 μm.

The charge transporting layer 5 provided on the charge generating layer 4 is formed by dissolving a charge transporting substance in wide use, such as a pyrazoline compound, a hydrazone compound, a styryl compound, a triphenylmethane compound, or a triphenylamine compound, in a suitable solvent along with a suitable binder having a film forming capacity, such as a polyester resin or a polycarbonate resin to prepare a coating solution, applying the coating solution, and drying the coated layer. The thickness of the charge transporting layer is preferably 5 to 50 μm. If desired, the charge transporting layer may contain various additives such as antioxidants.

Next, embodiments of the present invention will be described below.

EXAMPLE 1

Eighty parts by weight of alcohol-soluble 12/6/66 copolymeric polyamide (DAIAMID T-171, DAICEL-HÜLS LTD.) and 20 parts by weight of a styrene-maleic acid half ester copolymer (AF-20, BASF) were dissolved in an alcohol mixture of 70% by weight of methanol and 30% by weight of n-butanol to make 3% by weight of a solution. An aluminum pipe with an outside diameter of 60 mm, a length of 348 mm and a wall thickness of 1 mm was dipped in the resulting solution to coat its outside surface with the solution. The coating was dried to form an undercoating layer with a thickness of 0.5 μm.

Then, 2.1 parts by weight of an azo compound of the general formula (1), and 1.0 part by weight of a polyvinyl acetal (S-lec KS-1, Sekisui Chemical Co., Ltd.) were dispersed with 16 parts by weight of methyl ethyl ketone and 9 parts by weight of cyclohexanone in a sand mill. Further, 75 parts by weight of methyl ethyl ketone was added to make a coating fluid for forming a charge generating layer.

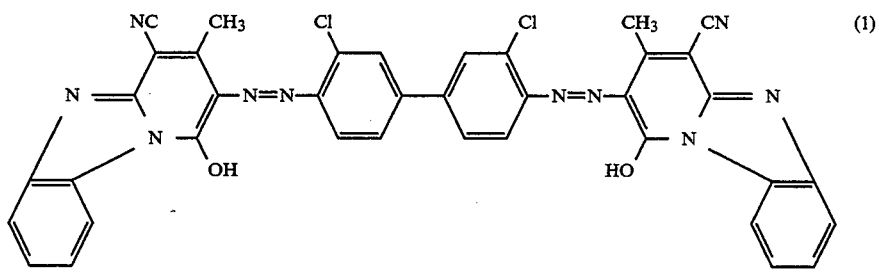

(1)

The coating fluid was dip coated onto the undercoating layer, and the coating was dried to form a charge generating layer with a thickness of 0.2 μm. Separately, 10 parts by weight of a hydrazone compound of the general formula (2) and 10 parts by weight of a polycarbonate (Iupilon PCZ-300, Mitsubishi Gas Chemical Co., Inc.) were dissolved in 80 parts by weight of tetrahydrofuran to obtain a coating solution. This coating solution was applied onto the charge generating layer, followed by drying the coating, to form a charge transporting layer with a thickness of 20 μm.

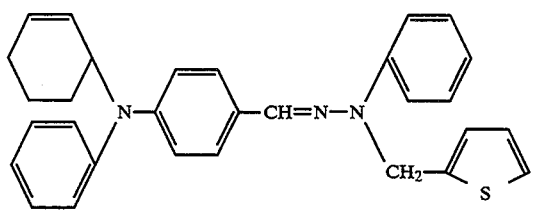

(2)

The so obtained photosensitive member was evaluated for electrophotographic characteristics using a commercially available copying machine (FP-3270, Matsushita Electric Industrial Co., Ltd.). The shadow potential Vd and the highlight potential Vi of the photosensitive member were initially set at −800 v and −100 v, respectively. The sensitivity $E_{\frac{1}{2}}$ was determined by the quantity of light (lx.s) required until exposure brought −800 v to −100 v. The potential when the luminous exposure was 10lx.s was designated as the residual potential Vr. Then, an endurance test in which the photosensitive member was charged to −800 v, and the charge was optically removed, was repeated 50,000 times. Thereafter, the shadow potential Vd, the highlight potential Vi, and the residual potential Vr were measured. The results are shown in Table 1.

TABLE 1

|  | Initial Properties | Properties after endurance test |
| --- | --- | --- |
| Vd (v) | −800 | −790 |
| Vi (v) | −100 | −110 |
| $E_{\frac{1}{2}}$ (lx.s) | 1.0 | 1.0 |
| Vr (v) | 30 | 40 |

As indicated in Table 1, the photosensitive member of Example 1 has high sensitivity, and its potential changes after the repeated cycles of charging and optical charge removal are minimal.

EXAMPLE 2

A photosensitive member was prepared in the same manner as in Example 1 except that the charge generating substance of the charge generating layer was replaced by a polycyclic quinone compound of the general formula (3).

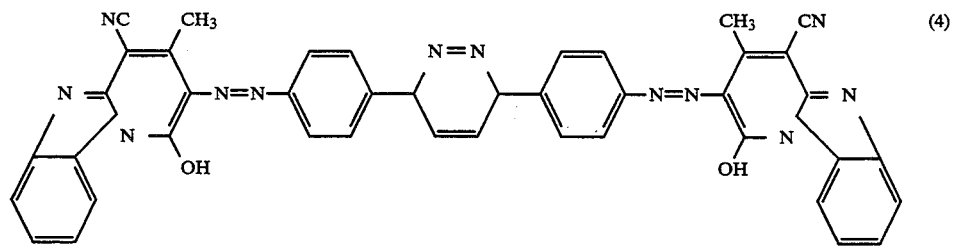

(3)

EXAMPLE 3

A photosensitive member was prepared in the same manner as in Example 1 except that the charge generating substance of the charge generating layer was replaced by an azo compound of the general formula (4).

(4)

COMPARATIVE EXAMPLES 1 TO 3

Photosensitive members of Comparative Examples 1, 2 and 3 were prepared in the same manner as in Examples 1, 2 and 3 except that no undercoating layer was provided.

The photosensitive members of Examples 2 and 3 and Comparative Examples 1, 2 and 3 were subjected to an endurance test repeated 50,000 times as in Example 1. The change in shadow potential (ΔVd), the change in highlight potential (ΔVi), the change in sensitivity (ΔE½), and the change in residual potential (ΔVr) of each photosensitive member after potential (ΔVr) of each photosensitive member after the test compared with the pretest state are shown in Table 2, including the data in Example 1. The photosensitive members of Examples 1 to 3 and Comparative Examples 1 to 3 were also evaluated for the quality of the resulting image before and after the endurance test. The results are included in Table 2.

TABLE 2

| Electrophotographic properties | | | | Quality of image | |
|---|---|---|---|---|---|
| ΔVd (v) | ΔVi (v) | ΔE½ (lx.s) | ΔVr (v) | Before | After |
| Ex. 1 | 10 | −10 | 0 | 10 | Good | Good |
| Ex. 2 | −5 | −5 | 0 | 3 | Good | Good |
| Ex. 3 | −5 | −5 | 0.05 | 4 | Good | Good |
| Comp. Ex. 1 | −100 | −50 | 0.4 | 40 | Good | Density decreased |
| Comp. Ex. 2 | −80 | −70 | 0.6 | 50 | Good | Density decreased |
| Comp. Ex. 3 | −60 | −100 | 0.8 | 60 | Good | Fogged |

As indicated in Table 2, the photosensitive members of the Comparative Examples after the repeated endurance test undergo considerable changes in properties and deterioration of image quality. The photosensitive members of the Examples involve minimal changes in properties, and their image quality is satisfactory and stable. Thus, the effect of the undercoating layer according to the present invention is evident.

The present invention has been described in detail with respect to preferred embodiments, and it will now be clear that changes and modifications may be made without departing from the invention in its broader aspects, and it is our intention, therefore, in the appended claims to cover all such changes and modifications as fall within the true spirit of the invention.

What is claimed is:

1. A photoconductor for electrophotography, comprising:
    an electroconductive substrate;
    an undercoating layer which is formed on the electroconductive substrate; and
    a photosensitive layer which is formed on the undercoating layer and which is comprised of a charge generating layer and a charge transporting layer, wherein the undercoating layer is comprised of 12/6/66 copolyamide and a styrene-maleic acid half ester copolymer, and wherein the 12/6/66 copolyamide is represented by general formula (I):

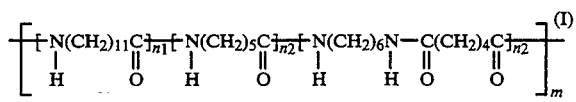

wherein $n_1$ denotes an integer of 10 to 50, $n_2$ denotes an integer of 25 to 45, and m denotes an integer of 1 to 20.

2. The photoconductor as claimed in claim 1, wherein the 12/6/66 copolyamide of general formula (I) is present in the undercoating layer in an amount ranging from 70 to 99% by weight.

3. The photoconductor as claimed in claim 1, wherein the charge generating layer comprises a charge generating substance comprised of at least one azo compound expressed by general formula II):

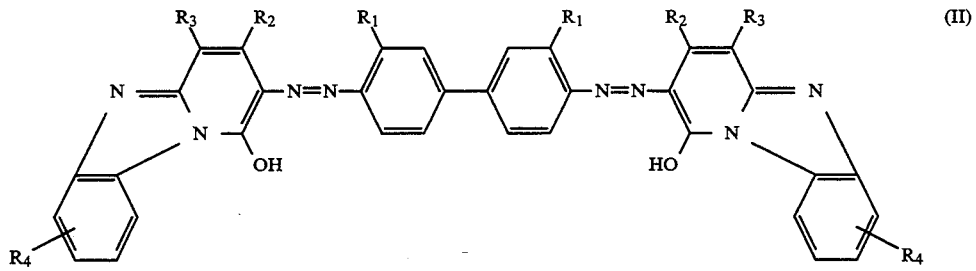

wherein $R_1$ represents a halogen atom, an alkyl group or an alkoxy group, $R_2$ represents an optionally substituted alkyl group, $R_3$ represents a hydrogen atom, a cyano group, a carbamoyl group, a carboxyl group, an ester group or an acyl group, and $R_4$ represents a hydrogen atom, a halogen atom, a nitro group, an alkyl group or an alkoxy group.

4. The photoconductor as claimed in claim 1, wherein the charge generating layer comprises a charge generating substance comprised of at least one polycyclic quinone compounds expressed by general formula (III):

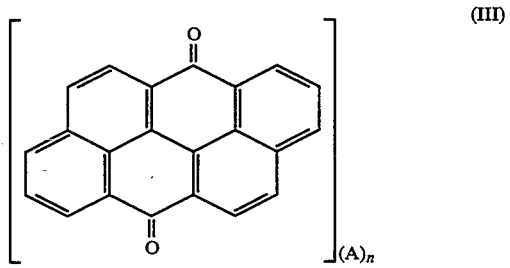

wherein A represents a halogen atom, a nitro group, a cyano group, an acyl group or a carboxyl group, and n denotes an integer of 0 to 4.

5. The photoconductor as claimed in claim 1, wherein the charge generating layer comprises at least one charge generating substance comprised of at least one azo compounds expressed by general formula (IV):

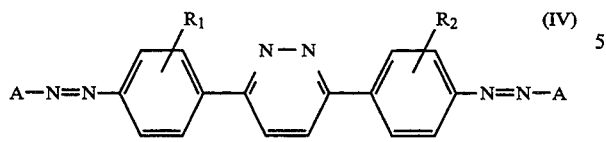

wherein A represents a coupler residue, and $R_1$ and $R_2$ each represent a hydrogen atom, a halogen atom, or an optionally substituted alkyl or alkoxy group.

6. The photoconductor as claimed in claim 1, wherein the charge generating layer comprises at least one charge generating substance comprised of at least one azo compound expressed by general formula (V):

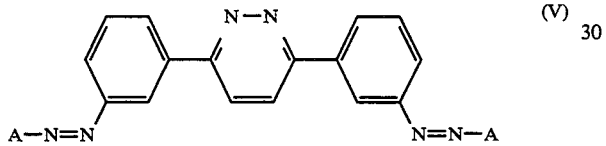

wherein A represents a coupler residue.

7. The photoconductor as claimed in claim 5, wherein the coupler residue A in general formula (IV) is a compound expressed by general formula (VI):

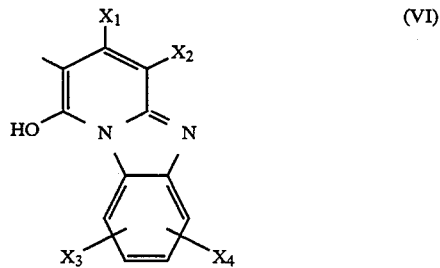

wherein $X_1$ represents an optionally substituted alkyl, aryl or heterocyclic group, $X_2$ represents a hydrogen atom, a cyano group, a carbamoyl group, a carboxyl group, an ester group, or an acyl group, and $X_3$ and $X_4$ each represent a hydrogen atom, a halogen atom, a nitro group, or an optionally substituted alkyl or alkoxy group.

8. The photoconductor as claimed in claim 6, wherein the coupler residue A in general formula (V) is a compound expressed by general formula (VI):

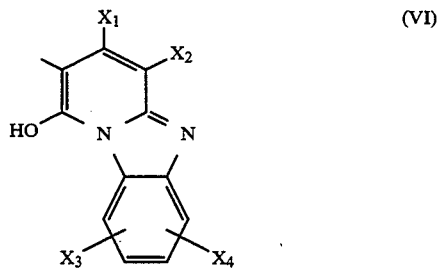

wherein $X_1$ represents an optionally substituted alkyl, aryl or heterocyclic group, $X_2$ represents a hydrogen atom, a cyano group, a carbamoyl group, a carboxyl group, an ester group, or an acyl group, and $X_3$ and $X_4$ each represent a hydrogen atom, a halogen atom, a nitro group, or an optionally substituted alkyl or alkoxy group.

* * * * *